United States Patent [19]

Wigness et al.

[11] Patent Number: 4,943,560
[45] Date of Patent: Jul. 24, 1990

[54] SOLVENT SYSTEM FOR CHRONIC VASCULAR INFUSION OF HYDROPHOBIC DRUGS

[75] Inventors: Bruce D. Wigness; Thomas D. Rohde, both of Minneapolis, Minn.

[73] Assignee: Regents of the University of Minnesota, Minneapolis, Minn.

[21] Appl. No.: 178,139

[22] Filed: Apr. 6, 1988

[51] Int. Cl.$^5$ .................... A61K 37/00; A61K 31/045
[52] U.S. Cl. ........................................ 514/11; 514/724
[58] Field of Search .................................. 514/11, 724

[56] References Cited

U.S. PATENT DOCUMENTS

| | | | |
|---|---|---|---|
| 3,731,681 | 5/1973 | Blackshear | 128/214 F |
| 4,108,985 | 8/1978 | Ruegger et al. | 514/11 |
| 4,439,181 | 3/1984 | Blackshear et al. | 604/56 |
| 4,998,823 | 1/1989 | Witzel | 514/11 |

OTHER PUBLICATIONS

*The Merck Index*, 10th Ed.(1983), p. 396, No. 2748.

Wigness et al., Chem. Abst. 105(9):85142g.
B. D. Wigness et al., *Trans. Am. Soc. Artif. Inter. Organs*, XXXI, 136–139, (1985).
Brange et al., *Properties of Insulin in Solution*, in Artificial Systems for Insulin Delivery (P. Brunetti 1983), at pp. 83–84. Lougheed et al., *Diabetologia*, 19, 1–9 (1980).
H. Buchwald et al., Implantable Infusion Pumps, *Year Book medical Publishers*, Inc., 177–221 at 185 (1984).

*Primary Examiner*—Douglas W. Robinson
*Assistant Examiner*—Kevin E. Weddington
*Attorney, Agent, or Firm*—Merchant, Gould, Smith, Edell, Welter & Schmidt

[57] ABSTRACT

The present invention provides a liquid infusate for the chronic vascular infusion of a hydrophobic biologically-active compound, such as cyclosporin, comprising a solution of a therapeutically-effective amount of the biologically-active compound in a mixture of about 10–80% glycerol and about 90–20% ethanol, by volume.

3 Claims, 5 Drawing Sheets a = Deionized Water
b = 95 % Ethanol
c = 40% Glycerol In Ethanol IN VIVO Testing Of Cyclosposin Infusion By Implantable Pump; Flow Rate Vs. Time

SOLVENT SYSTEM FOR CHRONIC VASCULAR INFUSION OF HYDROPHOBIC DRUGS

BACKGROUND OF THE INVENTION

When chronic administration of a pharmaceutically-active agent is required, vascular delivery via an external infusion pump, implantable infusion pump (IIP) or other vascular access device may be the dispensing means of choice. For example, IIP delivery may be preferred when either (a) the oral bioavailability of the agent is low (i.e., the drug is destroyed by gastrointestinal acids and enzymes or is not absorbed by the intestinal wall); (b) the therapeutic index of the drug is small (i.e., the dosage range between ineffectivity and toxicity is narrOw); (c) the in vivo half-life of the drug is short; or (d) the site of the delivery is important.

To realize the potential benefits of drug delivery by IIP, pharmaceutical preparations need to be designed to retain stability under environmental conditions not ordinarily encountered during storage and administration by conventional methods such as oral ingestion or parenteralinjection. These conditions include the surface properties of the materials used in IIP construction, the fluid dynamic variables that infusates are exposed to during transport through the devices, and the nature and amounts of the various gasses and fluids which permeate the device from the recipient's body.

Furthermore, drug formulations designed for parenteral delivery are generally designed for storage at temperatures other than physiological temperatures. Therefore, it is not unusual for a drug preparation, in the form that it is dispensed for conventional administration, to be incompatible with a particular pump. In such cases, either the pump, the drug molecule or the drug formulation must be modified to achieve reliable function of the IIP without compromising drug bioavailability.

A number Of pharmaceutical agents that might be delivered advantageously by implantable drug infusion pump or other vascular access means are insoluble in aqueous solutions. Some agents of this type are soluble in alcohols but alcohols may be unsuitable for use with certain types of infusion devices because of their carrying capacity for dissolved gasses, which can be rapidly released when the drug is delivered in vivo. For example, the vapor pressure-driven IIP disclosed by Blackshear et al. (U.S. Pat. No. 3,731,681) pumps a solution of a drug through 0.09 mm inner diameter capillary flow restrictors of lengths ranging from about 15 cm to more than 30 meters. Passage of the drug-containing infusate through the capillary catheter is accompanied by a pressure drop of approximately 20 kg/cm$^2$ due to the difference between drug reservoir pressure (23 kg/cm$^2$) and the venous or arterial blood pressure at the catheter tip. This pressure drop can be accompanied by the release of air bubbles from the infusates. This phenomenon, called outgassing, is determined by the vapor pressure and dissolved gas capacity of the solvent.

In the case of aqueous solutions, outgassing ordinarily does not result in air bubbles stopping the Blackshear et al. pump. However, if a pump is loaded with ethanol, which has seven times the capacity for air as does water under identical conditions of temperature and pressure, gas bubbles can form in the capillary flow restrictor. These bubbles collectively exert sufficient resistance to stop pump flow after less than 50 ml of infusate delivery.

Cyclosporin is one example of an important drug that is difficult to deliver via parenteral infusion because of its hydrophobicity. It is a powerful immunosuppressive drug that has improved graft survival in organ transplant recipients. In addition to its utility in organ transplantation, it may be effective in treating auto-immune diseases. Based on successful laboratory animal research, clinical pilot studies are now underway to test its ability to combat multiple sclerosis, lupus erythematosis, and rheumatoid arthritis. It may also prove effective to bring about remission of juvenile onset diabetes if given immediately after onset. Cyclosporin is also effective against such parasitic diseases as malaria and schistosomiasis.

Despite its advantages, the therapeutic index of cyclosporin is narrow so that dosages must be regulated within precise limits. The major side effect of cyclosporin is nephrotoxicity in 15 to 30% of patients. Therefore, a need exists for solvent systems which are useful to prepare infusates for the delivery of cyclosporin and other hydrophobic drugs via IIP, external infusion pumps, or other vascular access devices.

BRIEF DESCRIPTION OF THE INVENTION

The present invention is directed to a liquid infusate which is useful for the chronic vascular infusion of a hydrOphobic biologically-active compound. The infusate comprises a solution of a therapeutically-effective amount of the active compound in a solvent vehicle consisting essentially of about 10–80% glycerol and about 90–20% ethanol (about 4.0–0.1:1 v/v glycerol: ethanol), by volume. The use of the glycerol-ethanol solvent system provides stable solutions of a wide variety of hydrophobic biologically-active agents without the use of potentially deleterious solubilizing and stabilizing agents such as synthetic surfactants. Furthermore, the addition of glycerol to ethanol within the claimed concentration ranges has two other important effects: (a) it reduces the gas-carrying capacity of the solvent system below that exhibited by 95% ethanol, and (b) it increases the viscosity of the ethanol, thereby reducing the rate of release of any residual gas.

The present solvent systems do not contain significant amounts of water, other than the water present in the reagents as an impurity, e.g., they will contain no more than about 5% water by volume, if 95% ethanol is employed to form the infusate. Preferably, the liquid infusate of this invention will contain less than about 1% water by volume. As used herein, the term "ethanol" is intended to refer to 95% ethanol, which contains about 5% water, unless otherwise indicated.

The present invention is also directed to a method for the chronic vascular infusion of a hydrophobIc biologically-active compound to a human comprising: (a) dissolving a therapeutically effective amount of the biologically-active compound in a solvent consisting essentially of about 10–80% glycerol, preferably about 20–75%; and about 90–20%, preferably about 80–25% ethanol, by volume, to form an infusate solution, and (b) infusing said solution into the vascular system of the human. Preferably, after step (a), the infusate solution is introduced into the infusate storage chamber of a drug delivery device and, in step (b) the infusate is continuously discharged from the storage chamber through a water-impermeable, restricted flow passage into the blood stream of the patient, e.g., via a tubular passageway such as a cannula or a capillary catheter. Preferably, the drug delivery device will be a pressure activated pump which is affixed exterior to or implanted within the body of the human to whom the active compound is to be administered. Pumps suitable for implantation within the human body should be water-impermeable and include those disclosed in U.S. Pat. No. 3,731,681, and U.S. application Ser. No. 825,197,604/132 filed Feb. 3, 1986, the disclosures of which are incorporated by reference herein.

These are examples of pumps which are capable of providing a continuous, uniform fluid infusion from a storage chamber or internal reservoir. The latter is spring driven, while the former is vapor pressure driven. After implantation, these pumps can be recharged by injection of additional infusate into said reservoir through the skin of the human patient. As the infusion solution is discharged frOm the pump by a constant pressure exerted upon the reservoir, a restricted fluid passage imparts a low flow rate thereto. Electrically-driven external infusion pumps may also be used, and are reviewed in U.S. application Ser. No. 825,211, filed Feb. 3, 1986, the disclosure of which is incorporated by reference herein.

The "hydrophobic biologically-active compounds" useful in the present invention are those nonpolar drugs which are insoluble or only sparingly soluble in water at physiologic pH, but which dissolve in the present qlycerol-ethanol mixtures to the extent that the vascular infusion of no more than about 0.1-15 ml/day of the infusion solution will produce the desired therapeutic effect. Therefore, the infusate of the present invention will preferably be discharged at about 1-10 ml/day during the treatment period. The useful infusion solutions of the present invention comprising cyclosporin or a water-insoluble derivative thereof will contain about 25-500 mg/ml, preferably about 30-100 mg/ml of cyclosporin.

Percentages of components are by volume unless otherwise indicated.

DETAILED DESCRIPTION OF THE INVENTION

The present solutions were found to be particularly useful for the intravascular infusion of the hydrophobic immunosuppressive drug, cyclosporin. The delivery of therapeutically-effective amounts of cyclosporin by intravascular infusion in a substantially continuous, constant manner presents many of the problems associated with the intravascular infusion of hydrophobic bioactive compounds, particularly when the infusion is carried out from an infusate delivery device which has been implanted in vivo.

Structurally, cyclosporin is a cyclic polypeptide (m.w. 1,203) containing no charged functional groups. It is extremely hydrophobic but is very soluble in nonpolar solvents such as oils, alcohols and a variety of other organic solvents. For example, one gram of cyclosporin dissolves in one milliliter of 95% ethanol but precipitates readily upon the addition of small amounts of water. Unfortunately, 95% ethanol is not an acceptable solvent for the delivery of cyclosporin by many implantable infusion pumps and other intravascular access devices due to its high capacity for dissolved air which results in outgassing and plugging of the tiny fluid pathways of such devices.

Cyclosporin for intravenous administration is commercially-available as Sandimmune ™ IV (Sandoz Corp., Basel, Switzerland). This preparation contains ethanol and Cremophor ™ El (polyoxy-ethylated castor Oil, BASF) in a 1:2 ratio as the cosolvents. Sandimmune ™ IV is dispensed as a concentrate (50 mg/ml) which typically must be diluted twenty- to one hundred-fold wIth either 0.9% aqueous NaCl or 5% aqueous dextrose before administration by intravenous drip infusion. A twenty-fold dilution of Sandimmune ™ IV results in a cyclosporin concentration of only 2.5 mg/mI. At the currently prescribed therapeutic dose of 8 mg/kg/day, a patient of average physique is expected to require about 520 mg of cyclosporin daily (65 kg $\times$ 8 mg/kg/day=520 mg/day]. At 2.5 mg/ml, a person would require approximately 208 ml/day of total drug volume. This is more than four times the reservoir capacity of the largest commercially-available IIP.

The invention will be further described by reference to the following detailed examples.

EXAMPLE I.

Infusion of Cyclosporin Sandimmune ™ IV

Undiluted Sandimmune ™ IV is chemically and mechanically compatible with the Blackshear et al. IIP pump design. The pump does not become clogged due to the release of air bubbles and the drug is compatible with all of the components which make up the device. However, Sandimmune ™ IV was found to cause serious difficulties when infused intravenously in the undiluted form.

Figure 1:
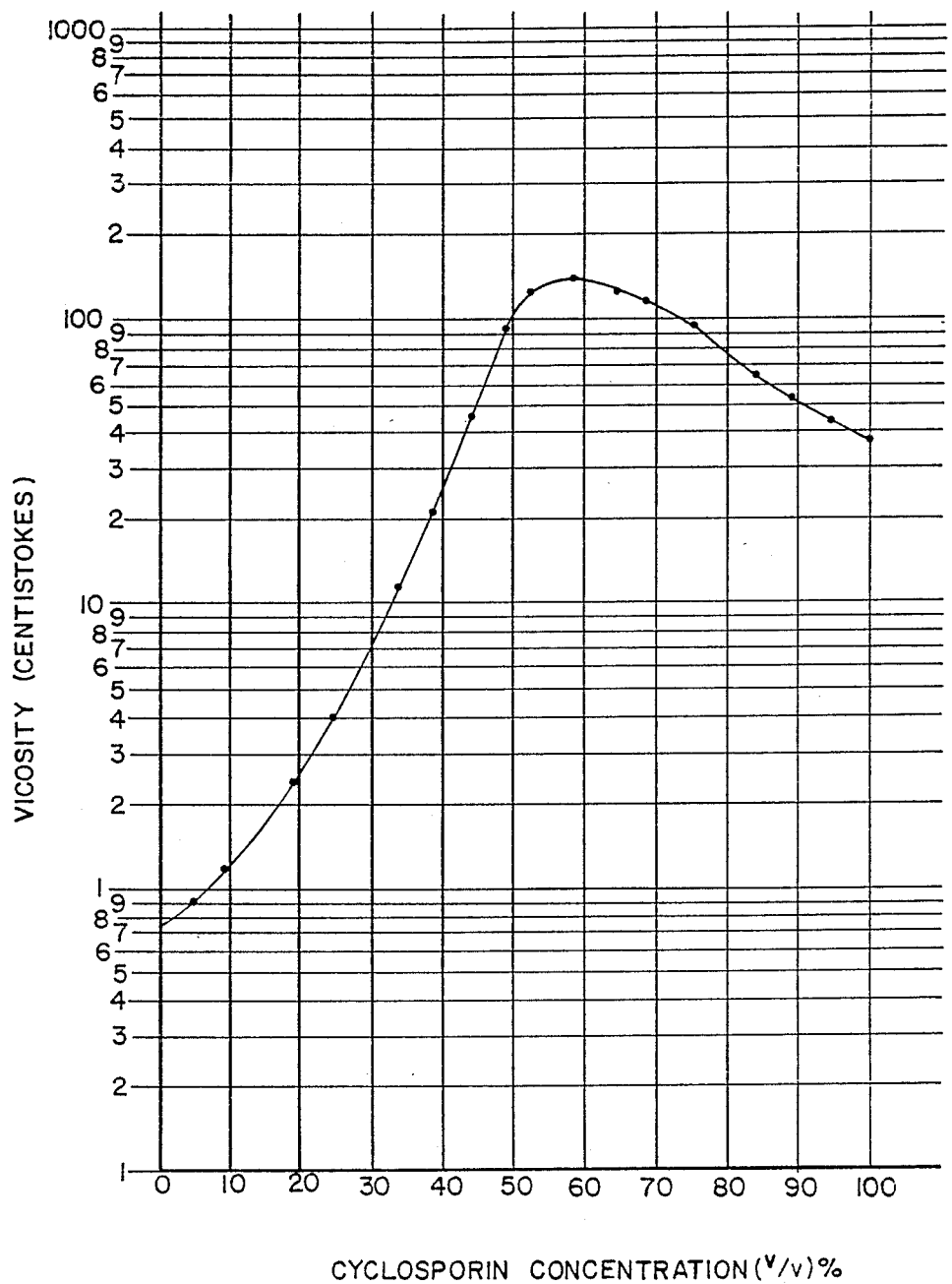
FIG. 1 is a graphical depiction of the viscosity profile of mixtures of Sandimmume ™ IV with normal saline.

The first difficulty is demonstrated in an in vitro experiment designed to model the mixing of drug with blood at the catheter tip. In this experiment, it was found that as Sandimmune ™ IV is diluted with normal saline, the viscosity gradually increases from 39 centipoise (100% Sandimmune ™ IV) to greater than 143 centipoise (b 60% Sandimmune ™ IV) before decreasing toward the viscosity of normal saline (0.7 centipoise) (FIG. 1).

Second, infusion of Sandimmune ™ IV by pump in the inferior vena cavas (IVC) of six dogs showed that good therapy could be achieved for only about four weeks before the pumps stopped flowing due to clot formation at the catheter tip. Furthermore, this clot was extensive enough to occlude the entire IVC. It is not known whether the phenomena of increasing viscosity and thrombus formation are related, but clearly, the use of this drug preparation in its concentrated form is limited.

EXAMPLE II.

Infusion of Cyclosporin in Ethanol Containing · $C_9H_{19}C_6H_4(OEt)_{14}OH$ The ingredient in Sandimmune ™ IV that is believed to be the cause of the drug's thrombogenicity and transient high viscosity is the nonionic surfactant Cremophor ™ El. Since Cremophor ™ El is a mixture of many different chemicals (e.g., polyethyleneqlycol ethers of the various fatty acids which are constituents of castor oil), the in vivo study of Example I was repeated, this time using polyethyleneglycol mono(-nonylphenyl) ether (Tergitol ™ NP-14, Sigma Chemical Co.) as the nonionic surfactant cosolvent mixed with 95% ethanol in a 2:1 v/v ratio. This solvent system is similar to the Cremophor ™ El-ethanol system used in Sandimmune ™ IV, but offers the advantage of containing only a single component surfactant. However, in two trials, both dogs died within 48 hours with grossly visible emboli in the lungs.

EXAMPLE III.

Evaluation and Infusion of Cyclosporin in Ethanol-Glycerol Mixtures

Figure 2:
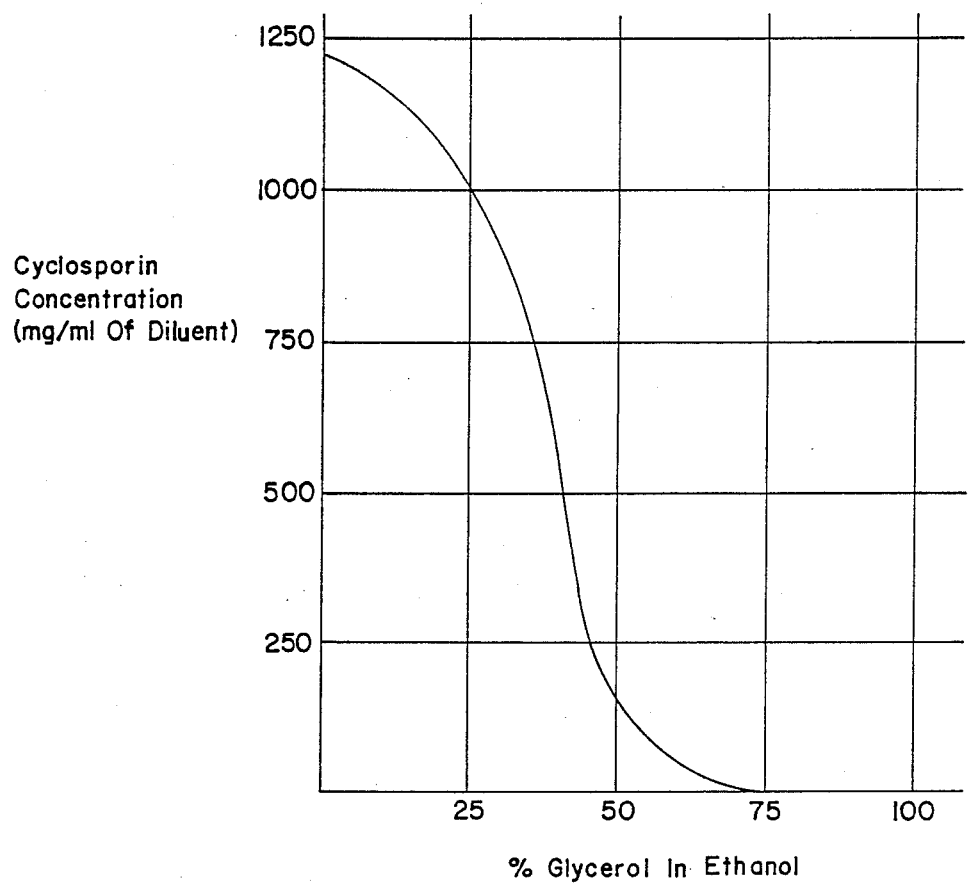
FIG. 2 is a graphical depiction of the solubility of cyclosporin in glycerol and in glycerol-ethanol mixtures.

The solubility of cyclosporin in glycerol and glycerol-ethanol mixtures which are surfactant-free is summarized in FIG. 2. The solubility of cyclosporin in mixtures of about 4.0–0.10:1 v/v qlycerol:ethanol was high enough to be therapeutically effective, while the solubility of air in these solvent systems was no more than its solubility in water.

The percent change in total gas pressure of deionized water, 95% ethanol and 95% ethanol containing 40% glycerol in response to the application of a 10 psig vacuum over 30 minutes was measured. The results of these measurements are plotted in FIG. 3 as the percent change in pressure vs. time.

Figure 3:
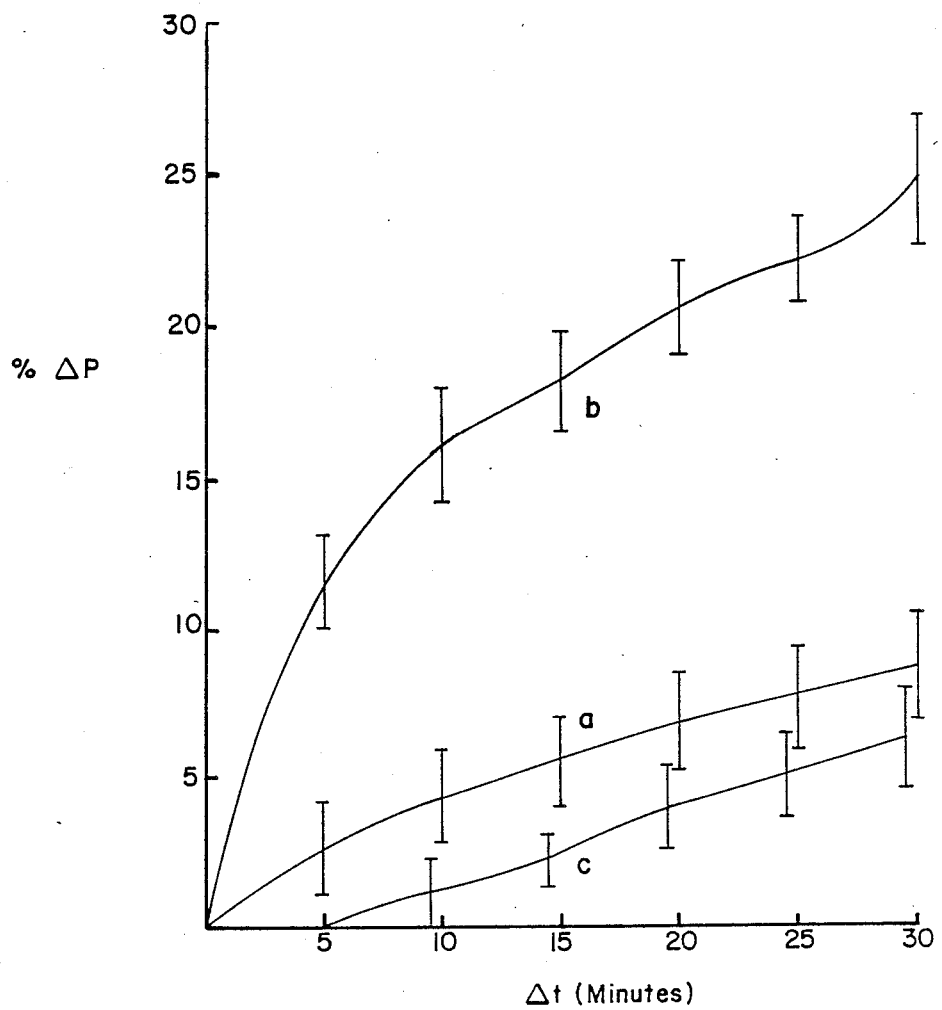
FIG. 3 is a graphical depiction of the percent volume of expelled air as a function of the concentration of glycerol in ethanol.

The data presented in FIG. 3 demonstrate that the amount of gas available to be released is lower in the case of water than in the case of ethanol, and is lower still when 40% qlycerol/60% ethanol is employed. Secondly, the rate of gas release is seen to be inversely proportional to the viscosity of the solution. In addition, the qlycerol-ethanol mixture exhibits a delayed gas release that indicates the presence of a supersaturated state that can exist for as long as 5 minutes.

Therefore, the addition of glycerol to ethanol has two important effects on a gas-containing solvent system: (a) it reduces the gas-carrying capacity of the solvent system and, (b) it increases the viscosity of the ethanol, thereby reducing the release rate of any residual gas.

Figure 4:
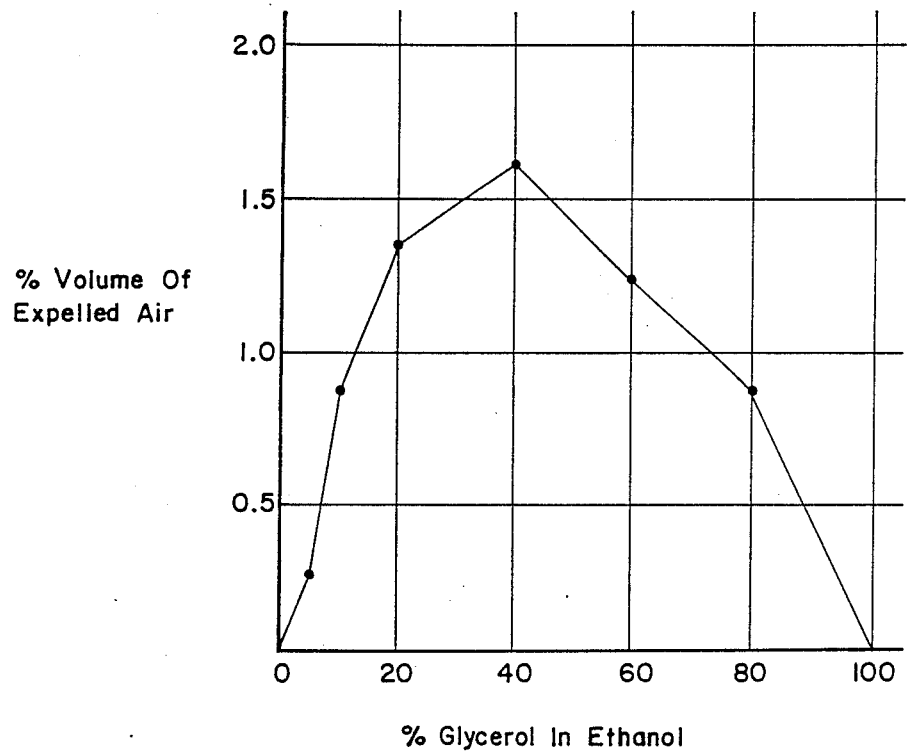
FIG. 4 is a graphical depiction of the percent change in pressure resulting from outgassing of (a) water; (b) 95% ethanol; and 40% glycerol in ethanol as a function of elapsed time after a 10 psig vacuum is applied to the fluid.

The glycerol also acts to reduce the amount of gas held in solution by the ethanol without substantially reducing the capacity of the ethanol to solvate the hydrophobic drug. As demonstrated by the data summarized in FIG. 4, there is an outgassing of ethanol that has been pre-saturated with gas when glycerol is added. The quantity of gas released increases in a substantially linear fashion as the percent of added glycerol increases.

Testing of 40% glycerol/60% ethanol at 37° C. in vitro demonstrated that the performance of the Blackshear et al. pump was as would be expected, given the viscosity of the infusate and the length of the capillary flow restrictor. However, in two dog trials, it was found that while both pumps functioned correctly when they were filled with a control infusate (40% glycerol/60% ethanol, and no cyclosporin), when they were filled with infusates containing (50 mg/ml ) cyclosporin, they stopped flowing within one week. The catheters were found to be completely occluded with a white material beginning immediately distal to the capillary-catheter junction. This material was presumed to be preCipitated cyclosporin which came out of solution due to the diffusion of trace amounts of moisture through the silicone rubber catheter wall and into the infusate.

This hypothesis was tested by an experiment in which two pumps infused 50 mg/ml cyclosporin diluted in 40% qlycerol/60% ethanol at 37° C. for one week, followed by one week in which the outflow catheter was placed into a beaker containing 0.9% NaCl. In this experiment, the delivered infusate was clear for the first part of the experiment, but became cloudy within one day of placing the catheter in saline and the pumps plugged within one week. This experiment was then repeated, except that the silicone rubber catheters (0.035" inner diameter, 0.090" outer diameter) were replaced with catheters which were lined with a Teflon ™ (polytetrafluoroethylene, 0.006" thick) tube. In this experiment, the delivered infusate remained clear and the flow rates of the pumps remained constant.

Figure 5:
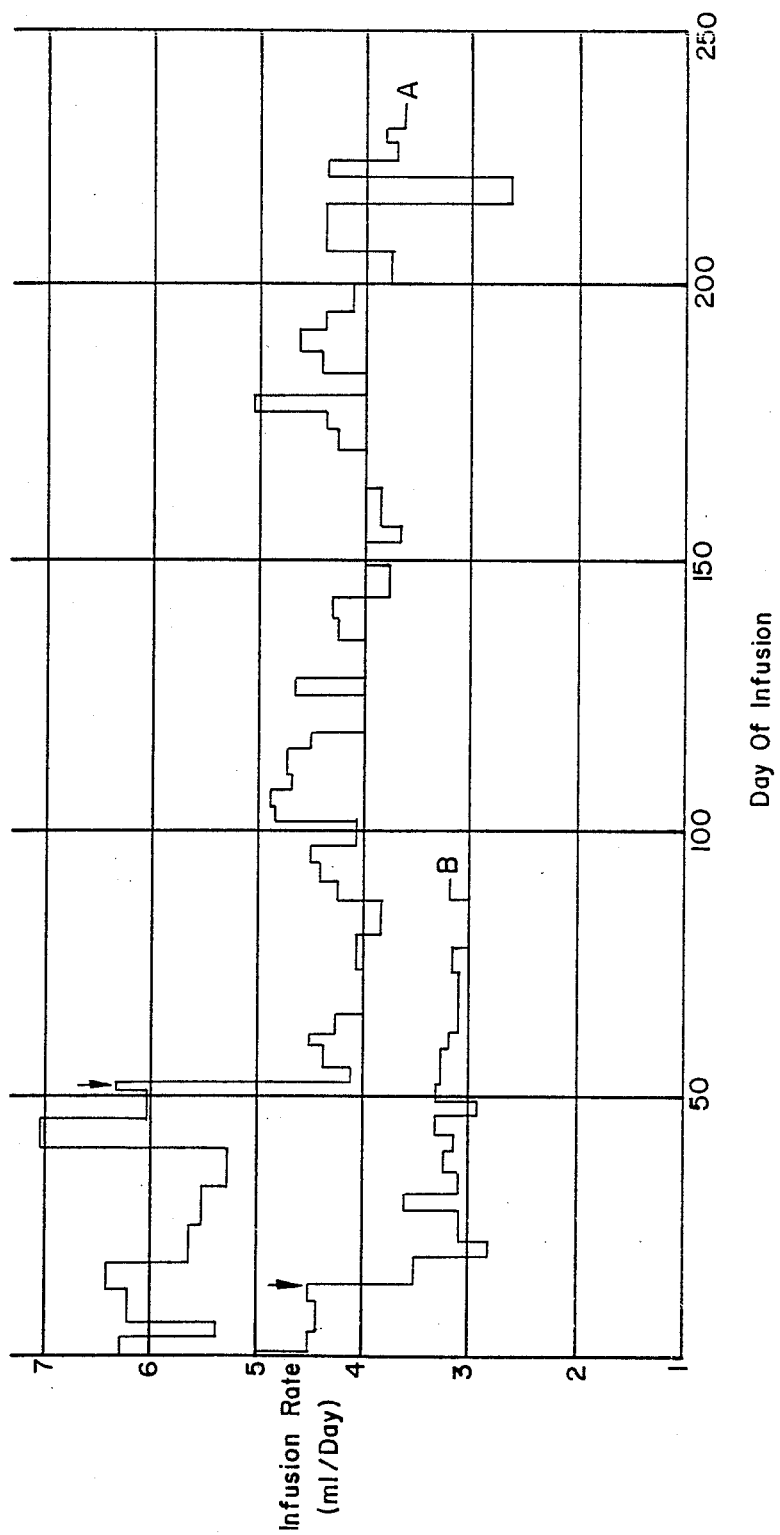
FIG. 5 is a graphical depiction of the infusion rates of solutions of cyclosporin in ethanol-qlycerol solutions via an IIP into dogs.

These pumps were then implanted in dogs and the results are summarized in FIG. 5. Trace A of FIG. 5 indicates the rate of infusion of a 48.4±7.0 mg/ml solution of cyclosporin in 2:3 v/v glycerol: ethanol. Trace B of FIG. 5 indicates the rate of infusion of a 35.4±4.0 mg/ml solution of cyclosporin in 2:3 v/v glycerol:ethanol. From the start of the cyclosporin infusion ( ↓ ) in each case, the rate remained substantially constant over the test period indicated.

The results of the in vivo experiments of Examples I–III are summarized in Table I, below.

TABLE I[1]

| In Vivo Testing of Cyclosporin Solvent Systems | | |
|---|---|---|
| Diluent | Months of[1] Infusion | Cause of Failure |
| EtOH/ Cremophor ™ El | 0.9 ± 0.1 (4) | Thrombus occlusion of the inferior vena cava. |
| EtOH/ Tergitol ™ | 0.1 ± 0.0 (2) | Death due to pulmonary embolism. |
| EtOH/ glycerol* | 0.3 ± 0.1 (2) | Cyclosporin precipitation in the catheter at the capillary-catheter junction. |
| EtOH/ glycerol** | Ongoing after 3 and 5 months. (2) | None. |

[1]The months of infusion are expressed as means ± one standard deviation (No. of trials).
*Silicone rubber catheter.
**Teflon-lined silicone rubber catheter.

The results summarized to Table I and in FIG. 5 demonstrate that the continuous infusion of therapeutically-effective doses of cyclosporin can be carried out indefinitely employing a water-impermeable infusion device and an ethanol-glycerol solvent system, without the use of nonionic surfactants.

Although the present invention has been described primarily by reference to cyclosporin as the biologically-active cOmpound, it is expected that the present solvent system and infusion method would be used to administer a wide variety of hydrophobic pharmaceutical agents including beta-blockers (e.g., propranolol, alprendol, oxprenolol, metoprolol), neuroleptics (e.g., penfluridol), aldosterone antagonists (e.g., sprinonolactone), chemosensitizers (e.g., benzidizole), antiarrthymics (e.g., quinidine, aprindine, amiodarone), barbiturates (e.g., rifampicin, phenytoin), and sedatives (e.g., benzodiazepines).

The concentration of a given hydrophobic biologically-active compound, the ratio of qlycerol to ethanol employed to form a stable infusate solution, and delivery parameters such as flow rate and loading volume can be readily determined by the physician, after consideration of such factors as the solubility of the active compound, the size and medical history of the patient, and the capabilities of the particular delivery system which is selected for use.

Therefore, although the invention has been described with reference to various specific and preferred embodiments and techniques, it should be understood that many variations and modifications may be made while remaining within the spirit and scope of the invention.

What is claimed is:

1. A liquid infusate for the chronic vascular infusion of a hydrophobic biologically-active compound comprising a solution of therapeutically-effective amount of a cyclosporin in a solvent consisting essentially of about 10–80% glycerol and about 90–20% ethanol, by volume.

2. The infusate of claim 1 which is free of nonionic surfactants.

3. The infusate of claim 1 which contains about 25–500 mg/ml cyclosporin.

* * * * *

UNITED STATES PATENT AND TRADEMARK OFFICE
CERTIFICATE OF CORRECTION

PATENT NO. : 4,943,560

DATED : July 24, 1990

INVENTOR(S) : Bruce D. Wigness et al.

It is certified that error appears in the above-identified patent and that said Letters Patent is hereby corrected as shown below:

At column 1, before the section "BACKGROUND OF THE INVENTION", insert the following section:

--GOVERNMENT SUPPORT
This invention was made with government support under POSCH grant 5R01-HL 15265 awarded by the National Institutes of Health. The government has certain rights in the invention.--

At column 1, line 16, for "narrOw" read --narrow--

At column 1, lines 23-24, for "parenteralinjection" read --parenteral injection--

At column 2, line 27, for "hydrOphobic" read --hydrophobic--

At column 3, line 7, delete "604/132" after --825,197,--

At column 3, line 16, for "frOm" read --from--

At column 3, lines 26-27, for "qlycerol" read --glycerol--

At column 3, line 36, for "mg/mI" read --mg/ml--

At column 3, line 52, after "and" insert --(c)--

At column 3, line 56, for "ethanol-qlycerol" read --ethanol-glycerol--

At column 4, line 24, for "wIth" read --with--

UNITED STATES PATENT AND TRADEMARK OFFICE
CERTIFICATE OF CORRECTION

PATENT NO. : 4,943,560

DATED : July 24, 1990

INVENTOR(S) : Bruce D. Wigness et al.

It is certified that error appears in the above-identified patent and that said Letters Patent is hereby corrected as shown below:

At column 4, line 28, for "mg/mI" read --mg/ml--

At column 4, line 31, for "mg/mI" read --mg/ml--

At column 4, line 55, for "(b 60%" read --(60%--

At column 5, lines 9-10, for "polyethyleneqlycol" read --polyethyleneglycol--

At column 5, lines 12-13, for "mono(-nonylphenyl)" read --mono-(nonylphenyl)--

At column 5, line 28, for "qlycerol:ethanol" read --glycerol:ethanol--

At column 5, line 41, for "qlycerol/60%" read --glycerol/60%--

At column 5, line 44, for "qlycerol-ethanol" read --glycerol-ethanol--

At column 6, line 5, for "preCipitated" read --precipitated--

At column 6, line 11, for "qlycerol/60%" read --glycerol/60%--

At column 6, line 55, for "to" read --in--

UNITED STATES PATENT AND TRADEMARK OFFICE
CERTIFICATE OF CORRECTION

PATENT NO. : 4,943,560

DATED : July 24, 1990

INVENTOR(S) : Bruce D. Wigness et al.

It is certified that error appears in the above-identified patent and that said Letters Patent is hereby corrected as shown below:

```
At column 6, line 63, for "cOmpound" read --compound--

At column 7, line 6, for "qlycerol" read --glycerol--
```

Signed and Sealed this

Twenty-sixth Day of March, 1996

Attest:

BRUCE LEHMAN

Attesting Officer

Commissioner of Patents and Trademarks